US00PP11502P

United States Patent [19]

Delbard

[11] Patent Number: Plant 11,502

[45] Date of Patent: Sep. 5, 2000

[54] HYBRID TEA ROSE PLANT NAMED 'DELSTRICYCLA'

[75] Inventor: Guy Delbard, Hyeres, France

[73] Assignee: Societe Anonyme des Pepinieres et Roseraies Georges Delbard, Commentry, France

[21] Appl. No.: 09/136,306

[22] Filed: Aug. 19, 1998

[51] Int. Cl.[7] ..... A01H 5/00

[52] U.S. Cl. ..... Plt./132

[58] Field of Search ..... Plt./130, 131, 132, Plt./143

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided that abundantly and nearly continuously forms attractive double flowers which are pink striped with white. The plant is well suited for cut flower production in the greenhouse. This blossom coloration is believed to be unique for greenhouse roses. The buds are large and ovate in configuration. The flowers exhibit a good vase life and possess petals that detach cleanly. The plant exhibits a bushy to upright growth habit, forms long straight stems and straight peduncles and forms vigorous vegetation. Additionally, the plant is resistant to diseases when grown under greenhouse conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) was an unnamed uncommercialized seedling. The male parent (i.e., the pollen parent) was the 'Krilamy' variety (non-patented in the United States). The parentage of the new variety can be summarized as follows:

Unnamed Seedling×'Krilamy'.

The seeds resulting from the above pollination were sown and 240 small plantlets were obtained which were physically and biologically different from each other. Selective study resulted in the identification of a single plant of the new variety.

It was found through careful study that the new variety of the present invention exhibits the following combination of characteristics:

(a) from a physical point of view forms green mature wood, assumes a bushy to upright growth habit, forms large ovate buds, and forms attractive long-lasting flowers that are pink striped with white and have consistent petals, and
(b) from the biological point of view forms vigorous vegetation, produces flowers in abundance on a nearly continuous basis, exhibits the ability readily to be forced, and is resistant to diseases when grown under greenhouse conditions.

The new variety well meets the needs of the horticultural industry and is particularly well suited for growing in the greenhouse for the production of attractive very long-lasting cut flowers that are pink striped with white.

The new variety can be readily distinguished from other varieties in view of the combination of characteristics described herein. It exhibits very long and straight stems, rigid and straight peduncles, a propensity to be forced under greenhouse growing conditions, and a long vase life for its distinctive pink striped with white blossoms.

The new variety has been found to undergo asexual propagation and can be readily reproduced by conventional routes, such as budding (i.e., eye grafting). This asexual reproduction by budding as performed at Hyéres, France, has demonstrated that the characteristics of the new variety are strictly transmissible from one generation to another and are firmly fixed.

The new variety has been named the 'Delstricycla' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

FIG. 1 — illustrates a specimen of a main branch;

FIG. 2 — illustrates a specimen of a flowering stem;

FIG. 3 — illustrates a specimen of a young shoot;

FIG. 4 — illustrates specimens of a leaf with three leaflets — plan view — upper surface;

FIG. 5 — illustrates a specimen of a leaf with five leaflets — plan view — upper surface;

FIG. 6 — illustrates a specimen of a leaf with seven leaflets — plan view — upper surface;

FIG. 7 — illustrates a specimen of a leaf with seven leaflets — plan view — under surface;

FIG. 8 — illustrates a specimen of a floral bud at the opening of the sepals;

FIG. 9 — illustrates a specimen of a floral bud at a more advanced stage than illustrated in FIG. 8;

FIG. 10 — illustrates a specimen of a floral bud at a more advanced stage than illustrated in FIG. 9;

FIG. 11 — illustrates a specimen of a floral bud at the opening of the petals;

FIG. 12 — illustrates a specimen of a floral bud in a more advanced stage of opening than as illustrated in FIG. 11;

FIG. 13 — illustrates a specimen of a floral bud at a more advanced stage of opening than as illustrated in FIG. 12;

FIG. 14 — illustrates a specimen of a flower as the opening progresses;

FIG. 15 — illustrates a specimen of an open flower-plan view — reverse;

FIG. 16 — illustrates a specimen of an open flower — plan view — obverse;

FIG. 17 — illustrates a specimen of a fully open flower — plan view — reverse;

FIG. 18 — illustrates a specimen of a fully open flower-plan view — obverse;

FIG. 19 — illustrates a specimen of a floral receptacle showing the arrangement of the stamens and pistils; and FIG. 20 — illustrates a specimen of a floral receptacle showing the arrangement of the pistils (stamens removed).

DETAILED DESCRIPTION

Figures 3, 4, 5, 6, 7, 8, 9, 10, 11, 12, 13, 14, 15, 16, 17, 18, 19, 20:
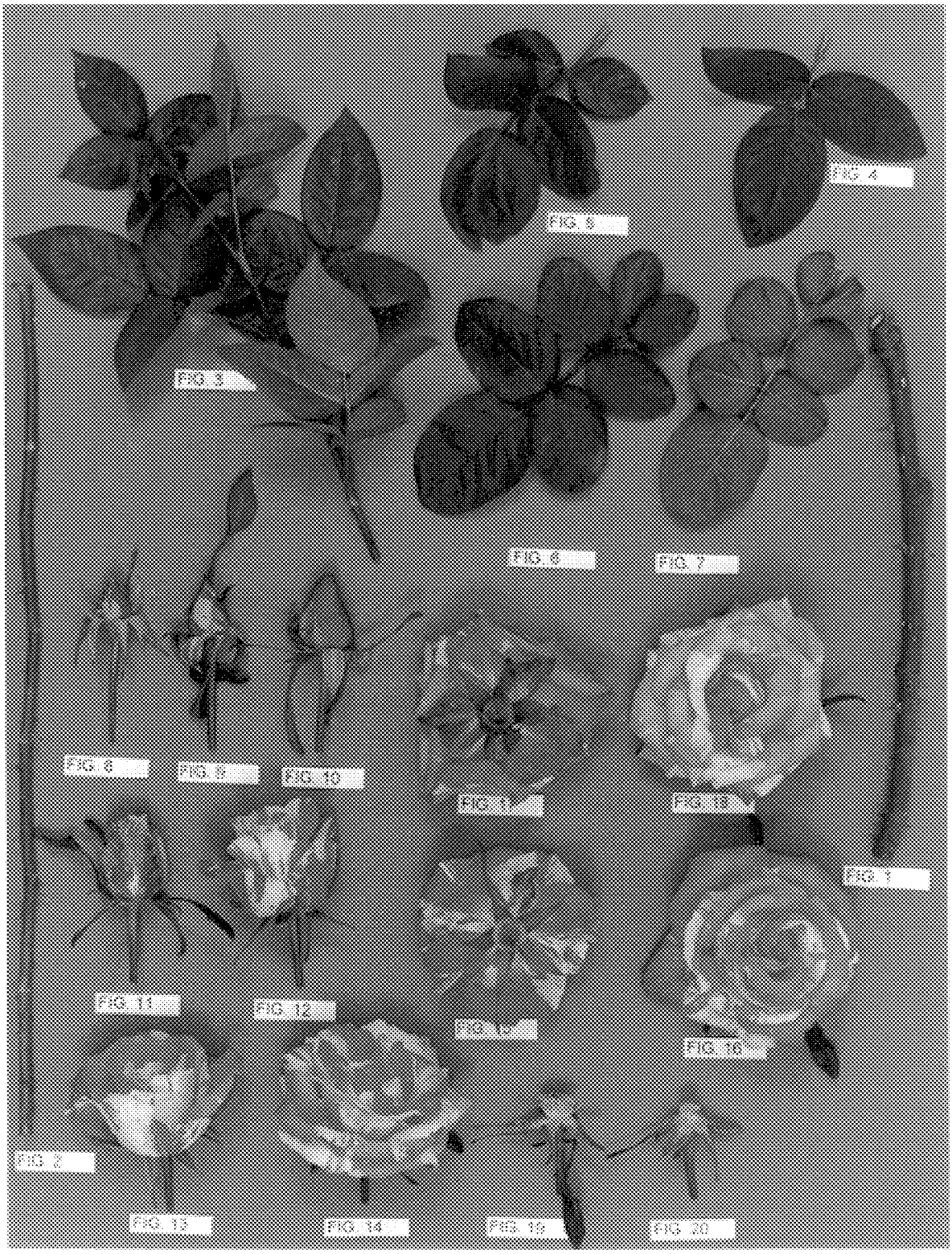

The chart used in the identification of the colors is that of The Royal Horticultural Society (R.H.S. Colour Chart). The description is based on the observation of plants grown under glass in the South of France. The coloration in common terms sometimes also is provided.

Class: Hybrid Tea.

Plant:

*Height.*—Plants which were pruned to a height of 80 cm. produce floral stems having a length of approximately 50 to 90 cm., and an average length of approximately 70 cm.

*Habit.*—Bushy to upright.

Branches:

*Color.*—Young shoots: When approximately 20 cm. long, exhibit a purple coloration, Greyed-Purple Group 183B at the tip changing to green, Yellow-Green Group 146C. Floral stems: Yellow-Green Group 146B. Mature wood: Yellow-Green Group 146A.

*Thorns.*—Configuration: Flat on the upper edge and concave on the under edge. Quantity, length and frequency: On a typical floral stem having a length of 10 cm., there commonly are approximately 3 small prickles <5 mm., and approximately 5 to 7 longer prickles >5 mm. On mature wood having a length of 10 cm., there commonly are approximately 15 to 18 pickles <5 mm. and approximately 5 to 7 longer pickles >5 mm. The length commonly is approximately 8 mm. on average on floral stems and approximately 9 mm. on average on mature wood. In each instance, the lengths commonly range from 1 to 11 mm. Color: On young shoots of approximately 30 cm. in length, the thorns are Greyed-Purple Group 183C to 183D, on floral stems the coloration of the thorns are Greyed-Yellow Group 162D with some reddish coloration, and on mature wood the thorns are Greyed-Orange Group 177B (Havana brown).

*Leaves.*—Number: Typical for the class. Size: Medium to large. Stipules: Adnate, small, and typical for the class.

*Leaflets.*—Number: Sometimes 3, and primarily 5 and 7. Size: Medium to large. Shape: Obtuse to rounded at the base of the terminal leaflet, slightly convex in cross section, and commonly possess weak margin undulation. Serration: Present, single, irregular, and very small. General appearance: Thin and weak with slight glossiness on the upper surface. Petiole: The inner surface is grooved with non-glandular edges. Petiole color on young shoot: Purple with green coloration on the inner surface and Yellow-Green Group 146D on the outer surface. Petiole color on floral stem: Bronze with green coloration on the inner surface and Yellow-Green Group 146D on the outer surface. Petiole color on mature wood: Yellow-Green Group 146D on inner surface, and Yellow-Green Group 146D on the outer surface. Petiole length of terminal leaflet: Approximately 12 to 19 mm., approximately 16 mm. on average, with a standard deviation of 2 mm. on a leaf of five leaflets. Terminal leaflet length: Approximately 45 to 100 mm., approximately 68 mm. on average, with a standard deviation of 10 mm. Terminal leaflet width: Approximately 33 to 55 mm., approximately 50 mm. on average, with a standard deviation of 5 mm. Terminal leaflet shape at base: Obtuse to rounded. Leaflet color of young shoot: On the upper surface Greyed-Purple Group 183B with some green coloration on the first leaves, and then green with reddish coloration on the margin changing to Yellow-Green Group 146B, and on the under surface Greyed-Purple Group 183B on the first leaves, and then purple with greenish coloration changing to Yellow-Green Group 147C. Leaflet color on floral stem: Yellow-Green Group 147A on the upper surface and Yellow-Green Group 148B on the under surface. Leaflet color of mature wood: Yellow-Green Group 147A on the upper surface, and Yellow-Green Group 148B on the under surface.

Inflorescence:

*Number of flowers.*—Generally one to five per stem as the auxiliary buds form flowers when grown under forced greenhouse conditions.

*Peduncle.*—Erect, stiff, Yellow-Green Group 146A with no hairs, commonly approximately 11 to 15 cm. in length (approximately 12 cm. in length on average).

*Sepals.*—Configuration: Two sepals commonly possess no extensions, and three sepals commonly possess extensions. The sepal length commonly ranges from approximately 30 to 60 mm. on average. Color: Yellow-Green Group 146B to 146C on the upper surface and Yellow-Green Group 146A to 146B on the under surface.

*Buds.*—Shape: Ovate. Size before calyx breaks: The bud lengths are approximately 21 to 30 mm., with an average length of approximately 23 mm. Color as calyx breaks: Red-Purple Group 60A striped with greenish-cream coloration. Size after calyx breaks: The bud lengths are approximately 44 to 60 mm., with an average length of approximately 47 mm. Color after calyx breaks: Inside: Red-Purple Group 63B to 63C and irregularly striped with white. Outside: Red-Purple Group 63A to 63B and irregularly striped with white.

*Flower.*—Time: Nearly continuously flowering. Shape: Double. Form: Round to irregularly rounded when viewed from above, flattened at the upper part when viewed from the side, and flattened convex at the lower part when viewed from the side. Diameter: Medium to large, approximately 9.2 to 11.8 cm., and approximately 10 cm. on average, with a standard deviation of 0.8 cm. Petal number: Commonly approximately 30 to 38, and an average of approximately 35. Petal size (second row from outside): The length is approximately 43 to 54 mm., a mean of approximately 51 mm., and a standard deviation of 2 mm.; and the width is approximately 46 to 52 mm., a mean of approximately 50 mm., and a standard deviation of 2 mm. Petal shape: Nearly rounded with medium reflexing of the margin and medium undulation of the margin. Petal color: The following description of a nearly fully open flower was made while observing a rose grown in the greenhouse during May which had been undergoing opening for two days. Petal color (middle zone): On the inner surface Red-Purple Group 63C to 63D towards the point of attachment an sometimes pink with irregular white stripes, and on the outer surface Red-Purple Group 63B to 63C and sometimes pink with irregular white stripes. Petal color (marginal zone): On the inner surface Red-Purple Group 63A to 63B and sometimes deeper Red-Purple Group 61B depending on the weather and sometimes irregular stripes of White Group 155B and sometimes pink with white, and on the outer surface Red-Purple Group 63C and sometimes irregular stripes of White Group 155B and sometimes pink with white. Petal spot at base: Small in size. Color of spot inner side: Yellow Group 3C. Color of spot outer side: Yellow-Green Group 150C. Stamens: Approximately 80 in number and are somewhat regularly arranged around the pistils. Filaments: Medium in length and Yellow Group 6C in coloration. Anthers: Medium in size, each opens at approximately the same time, and the immature coloration is Yellow Group 12B. Pollen: Normal in quantity and Yellow Group 4D in coloration. Pistils: Approximately 60 in number. Styles: Medium in length and Yellow-Green Group 154D in coloration. Stigmas: Yellow-Orange Group 14C, and generally are present at the same level as the anthers. Hips: No hips have been observed to date under greenhouse growing conditions. Seeds: None to date. Petal drop: Petals detach cleanly. Fragrance: None. Productivity: Under standard greenhouse growing conditions in the South of France commonly produces approximately 130 to 150 flowers per square meter per year. Lasting quality: Very good. When cut and placed in a vase, the flowers commonly last approximately 8 days. When present on the plant, the flowers commonly last approximately 8 to 10 days.

Development:

*Vegetation.*—Vigorous.

*Blooming.*—Abundant and almost continuous.

*Aptitude to forcing.*—Good.

*Resistance to diseases.*—Good under greenhouse conditions, and is sensitive to powdery mildew when grown outdoors.

I claim:

1. A new and distinct variety of Hybrid Tea rose plant characterized by the following combination of characteristics:

(a) from a physical point of view forms green mature wood, assumes a bushy to upright growth habit, forms large ovate buds, and forms attractive long-lasting flowers that are pink striped with white and have consistent petals, and (b) from the biological point of view forms vigorous vegetation, produces flowers in abundance on a nearly continuous basis, exhibits the ability readily to be forced, and is resistant to diseases when grown under greenhouse conditions;

substantially as herein shown and described.

* * * * *